United States Patent
Selim

(10) Patent No.: US 11,577,058 B2
(45) Date of Patent: Feb. 14, 2023

(54) CARDIOPULMONARY RESUSCITATION CATHETER AND RELATED SYSTEMS AND METHODS

(71) Applicant: Regents of the University of Minnesota, Minneapolis, MN (US)

(72) Inventor: Ahmed Selim, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 818 days.

(21) Appl. No.: 16/237,799

(22) Filed: Jan. 2, 2019

(65) Prior Publication Data

US 2019/0255301 A1 Aug. 22, 2019

Related U.S. Application Data

(63) Continuation of application No. 15/066,819, filed on Mar. 10, 2016, now Pat. No. 10,188,837.

(60) Provisional application No. 62/130,838, filed on Mar. 10, 2015.

(51) Int. Cl.

| A61M 25/10 | (2013.01) |
| A61M 1/16 | (2006.01) |
| A61M 1/36 | (2006.01) |
| A61M 39/08 | (2006.01) |

(52) U.S. Cl.
CPC ...... *A61M 25/1011* (2013.01); *A61M 1/1698* (2013.01); *A61M 1/3613* (2014.02); *A61M 1/3666* (2013.01); *A61M 1/3667* (2014.02); *A61M 2025/1052* (2013.01); *A61M 2039/082* (2013.01)

(58) Field of Classification Search
CPC ............ A61M 25/1011; A61M 1/3613; A61M 1/3667; A61M 1/1698; A61M 1/3666; A61M 2025/1052; A61M 2039/082
USPC ..................................................... 604/99.01
See application file for complete search history.

(56) References Cited

U.S. PATENT DOCUMENTS

| 5,216,032 A | 6/1993 | Manning |
| 5,437,633 A | 8/1995 | Manning |
| 5,678,570 A | 10/1997 | Manning |
| 5,716,318 A | 2/1998 | Manning |
| 6,117,105 A * | 9/2000 | Bresnaham ........ A61M 25/1011 604/509 |
| 2014/0142548 A1 | 5/2014 | Manning et al. |

* cited by examiner

*Primary Examiner* — Phillip A Gray
(74) *Attorney, Agent, or Firm* — Dentons Davis Brown; Matthew Warner-Blankenship

(57) ABSTRACT

The disclosed device, systems and methods relate to a novel catheter, system and methods. Exemplary embodiments comprise a plurality of lumens and balloons for insertion into the aorta and vena cava.

17 Claims, 13 Drawing Sheets

CARDIOPULMONARY RESUSCITATION CATHETER AND RELATED SYSTEMS AND METHODS

CROSS-REFERENCE TO RELATED APPLICATION(S)

This application is a continuation of U.S. application Ser. No. 15/066,819, filed Mar. 10, 2016, which claims the benefit under 35 U.S.C. § 119(e) to U.S. Provisional Application 62/130,838, filed Mar. 10, 2015, both of which are entitled "Cardiopulmonary Resuscitation Catheter and Related Systems and Methods," and are hereby incorporated herein by reference in their entirety.

FIELD OF THE INVENTION

The various embodiments disclosed herein relate to catheters for use as medical devices, and more particularly to catheters for use in cardiopulmonary resuscitation and other medical or surgical conditions that require emergency restoration of cerebral and cardiac blood supply.

BACKGROUND

The disclosed relates to devices, systems and methods relating to uses in cardiopulmonary resuscitation and other cardiological and pulmonary applications. More specifically, the various embodiments and implementations relate to a novel catheter, system and methods of use for occlusion and perfusion of a region of the circulatory system.

Cardiopulmonary resuscitation ("CPR") by external chest compression, represents an area that has experienced little progress over the last 50 years. Despite relatively poor outcomes, physicians continued to perform the same technique in resuscitating cardiac arrest patients without any substantial changes.

One major downside of using early CPR is the inability to deliver blood supply with sufficient perfusion pressure to the brain. While the primary goal of early CPR is to provide oxygenated blood to the brain and cardiac muscle in order to prevent the deleterious sequelae of brain ischemia and to facilitate a fast return of normal cardiac function, the current resuscitation procedures are inadequate in both tasks. Reports abound of poor post-resuscitation survival rates and poor neurological outcomes for those who survive. Patients who undergo chest compression for over 20 minutes are less likely to survive without neurological deficits, which means there is only a narrow window for intervention before a permanent damage takes place.

Extracorporeal membrane oxygenation ("ECMO") is an established procedure that has shown promising results in patients with cardiac arrest. Using ECMO in CPR ("ECPR") was associated with improved outcomes compared to conventional CPR with significantly better survival to hospital discharge, better neurological outcomes and better long-term survival. Nevertheless, ECMO and ECPR require a highly trained team for implementation. Additionally, supporting the circulation with ECMO entails the placement of multiple large bore vascular access catheters of up to 10 mm in diameter. These large bore catheters can only be placed by healthcare professionals with very high level of training and extensive expertise. Further, ECMO teams are only available in highly equipped medical centers, which inherently limits ECMO use in addressing events outside of these settings.

For example, trauma is estimated to cause over five million deaths every year worldwide, with bleeding considered to be the leading preventable cause of death. The disclosed catheter has the potential to save the lives of traffic accident patients who have active bleeding by maintaining the heart and brain perfusion until the patient can get a definitive intervention. Similarly, limited ECMO might be useful in battlefield hospitals, where there is a great need to provide a temporary support to the vital organs' circulation in a bleeding patient until transportation is available. Other uses for the disclosed embodiments include major vascular surgical procedures, where creating an isolated vascular compartment is helpful, and as a back-up circulatory support in high-risk coronary artery interventions.

Accordingly, there is a need in the art for improved means of resuscitation. The various implementations can help to improve these outcomes.

BRIEF SUMMARY

Discussed herein are various embodiments of a catheter, system and methods. In exemplary embodiments, the catheter comprises at least one lumen and at least one balloon.

The disclosed system is a catheter that can be rapidly introduced into the body through a variety of established methods, such as through a femoral artery puncture to the aorta. The disclosed catheter selectively provides pressure controlled, oxygenated blood to the vessels that supply the heart and brain.

The disclosed implementations relate to devices, systems and methods for providing temporary circulatory support in situations such as cardiac arrest for patients. The disclosed embodiments can be used to maintain circulation to vital organs until the patient can be transferred to a higher level of care. In various implementations, the disclosed catheters are smaller than conventional ECMO, and hence easier to use by healthcare personnel with average training.

In Example 1, an aortic catheter comprising a first elongate, substantially tubular primary aortic lumen having proximal and distal ends and comprising at least one aortic opening at the distal end; at least one elongate substantially tubular supplemental aortic lumen constructed and arranged to extend substantially past the distal aortic opening; and at least one aortic balloon in operational communication with the at least one supplemental aortic lumen so as to be inflated by way of the supplemental aortic lumen.

In Example 2, the aortic catheter of Example 2, further comprising a pressure sensor constructed and arranged to measure pressure in the aorta or inferior vena cava.

In Example 3, the aortic catheter of Example 1, further comprising a vena cava catheter constructed and arranged to be disposed within the vena cava of the patient and comprising a first elongate, substantially tubular primary venous lumen having proximal and distal ends and comprising at least one venous opening at the distal end; at least one elongate substantially tubular supplemental venous lumen constructed and arranged to extend substantially past the distal venous opening; and at least one venous balloon in operational communication with the at least one supplemental venous lumen so as to be inflated by way of the supplemental venous lumen.

In Example 4, the aortic catheter of Example 3, further comprising a pressure sensor constructed and arranged to measure pressure in the aorta or inferior vena cava.

In Example 5, the aortic catheter of Example 3, constructed and arranged for perfusing the heart of the patient via a control unit in operational communication with the catheters.

In Example 6, the aortic catheter of Example 3, wherein the control unit is constructed and arranged to provide blood in response to the measured pressure.

In Example 7, the aortic catheter of Example 4, wherein the inflation and deflation of at least one of the aortic balloon or the venous balloon can be controlled by the pressure sensor.

In Example 8, a cardiopulmonary resuscitation catheter system for use in a patient to permit isolation of a portion of the vascular system of the patient, the system comprising a resuscitation catheter comprising an elongate catheter shaft defining a first elongate, substantially tubular primary lumen having proximal and distal ends and comprising at least one opening at the distal end; and at least one balloon in operational communication with the elongate catheter shaft and constructed and arranged so as to be inflated; and a control unit comprising an air pump in hermetic communication with the at least one balloon, wherein the elongate catheter shaft is constructed and arranged to be disposed within the vena cava of the patient, the control unit is constructed and arranged to inflate the at least one balloon to a specified pressure, and the pressure sensor is constructed and arranged to measure pressure in the aorta or inferior vena cava of the patient such that the inflation and deflation of the at least one balloon can be controlled by the control unit.

In Example 9, the system of Example 8, further comprising at least one elongate substantially tubular supplemental lumen.

In Example 10, the system of Example 9, wherein the at least one elongate substantially tubular supplemental lumen is constructed and arranged to be disposed within the primary lumen.

In Example 11, the system of Example 9, wherein the at least one balloon is in operational communication with the at least one elongate substantially tubular supplemental lumen and inflated by way of the supplemental lumen.

In Example 12, the system of Example 8, further comprising a pressure sensor in operational communication with the control unit.

In Example 13, the system of Example 8, wherein the at least one balloon comprises a circumferential balloon disposed outside the primary lumen and is constructed and arranged to be inflated in the descending aorta of the patient.

In Example 14, the system of Example 13, wherein the second balloon is constructed and arranged to be passed into the ventricular cavity of the patient and inflated.

In Example 15, the system of Example 13, wherein the control unit is constructed and arranged to inflate and deflate the first balloon and/or second balloon in response to changes in blood pressure.

In Example 16, the catheter of Example 12, further comprising at least one valve in operational communication with the at least one balloon and at least one supplemental lumen, wherein the at least one valve is constructed and arranged to allow passage of fluid or gas into the at least one balloon for inflation and deflation.

In Example 17, the catheter of Example 12, wherein the catheter is constructed and arranged to be disposed within the vena cava of the patient.

In Example 18, a cardiopulmonary resuscitation system, comprising an elongate, tubular catheter constructed and arranged to be inserted through the aortic valve of the patient comprising an elongate primary lumen, comprising a proximal primary lumen end; a distal primary lumen end; and at least one opening at the distal primary lumen end; at least one elongate supplemental lumen disposed within the primary lumen, the supplemental lumen comprising a proximal supplemental lumen end; and a distal supplemental lumen end; a first balloon disposed outside the primary lumen and adapted for inflation; and a second balloon in operational communication with the supplemental lumen; and an external control unit.

In Example 19, the system of Example 18, wherein the elongate, tubular catheter is constructed and arranged for positioning the opening within the descending aorta of the patient; inflating the first balloon within the descending aorta of the patient via the external control unit; and inflating the second balloon distally of the right and left coronary arteries of the patient.

In Example 20, the system of Example 19, wherein the tubular catheter is further constructed and arranged for regulating the inflation of the first balloon and second balloon in response to changes in blood pressured measured by a pressure sensor.

One Example includes a catheter for use in a patient, including: a first elongate, substantially tubular primary lumen having proximal and distal ends and including at least one opening at the distal end; at least one elongate substantially tubular supplemental lumen configured to be disposed within the primary lumen and extend substantially past the distal opening; and at least one balloon in operational communication with the at least one supplemental lumen so as to be inflated by way of that lumen.

Implementations may include one or more of the following features. The catheter where the at least one balloon includes a first balloon and a second balloon. The catheter where the first balloon is a circumferential balloon disposed outside the primary lumen and is configured to be inflated in the descending aorta of the patient. The catheter where the second balloon is configured to be passed into the ventricular cavity of the patient and inflated. The catheter further including at least one valve in operational communication with the at least one balloon and at least one supplemental lumen, where the at least one valve is configured to allow passage of fluid or gas into the at least one balloon for inflation and deflation. The catheter where the catheter is configured to be disposed within the vena cava of the patient.

Implementations of the described techniques and control unit may include hardware, a method or process, or computer software on a computer-accessible medium. Other embodiments of this Example include corresponding computer systems, apparatus, and computer programs recorded on one or more computer storage devices, each configured to perform the actions of the methods. Other embodiments of this Example include corresponding computer systems, apparatus, and computer programs recorded on one or more computer storage devices, each configured to perform the actions of the methods. Implementations of the described techniques may include hardware, a method or process, or computer software on a computer-accessible medium.

Another Example includes a system for cardiopulmonary resuscitation of a patient, including: an elongate, tubular catheter, including: in elongate, substantially tubular primary lumen, including: a proximal primary lumen end; a distal primary lumen end; and at least one opening at the distal primary lumen end; at least one elongate substantially tubular supplemental lumen including a proximal end and a distal end, where the at least one supplemental lumen is configured to be disposed substantially within the primary lumen and extend substantially past the distal opening of the outer lumen into the patient; and a first balloon disposed outside the primary lumen and adapted for inflation.

Another Example includes an occlusion and perfusion system for use in patient resuscitation, including: a first catheter configured to be disposed within the aorta of the patient, including: a first elongate, substantially tubular primary aortic lumen having proximal and distal ends and including at least one aortic opening at the distal end; at least one elongate substantially tubular supplemental aortic lumen configured to extend substantially past the distal aortic opening; and at least one aortic balloon in operational communication with the at least one supplemental aortic lumen so as to be inflated by way of the supplemental aortic lumen; and a second catheter configured to be disposed within the vena cava, including: a first elongate, substantially tubular primary venous lumen having proximal and distal ends and including at least one venous opening at the distal end; at least one elongate substantially tubular supplemental venous lumen configured to extend substantially past the distal venous opening; and at least one venous balloon in operational communication with the at least one supplemental venous lumen so as to be inflated by way of the supplemental venous lumen, where the first and second catheters are configured to be disposed with the body of the patient so as to occlude an perfuse the heart of the patient.

Implementations of these Examples may include one or more of the following features. The catheter where the at least one balloon includes a first balloon and a second balloon. The catheter where the first balloon is a circumferential balloon disposed outside the primary lumen and is configured to be inflated in the descending aorta of the patient. The catheter where the second balloon is configured to be passed into the ventricular cavity of the patient and inflated. The catheter further including at least one valve in operational communication with the at least one balloon and at least one supplemental lumen, where the at least one valve is configured to allow passage of fluid or gas into the at least one balloon for inflation and deflation. The catheter where the catheter is configured to be disposed within the vena cava of the patient. The system further including a second balloon. The system where the first balloon and second balloon are circumferential balloons. The system further including a substantially tubular second supplemental lumen further including proximal and distal ends, where the at least second supplemental lumen is configured to be disposed substantially within the outer lumen and extend substantially past the distal opening of the outer lumen into the patient. The system where the second supplemental lumen is configured to accommodate the passage of tools into the patient. The system further including a control unit. The system where the control unit includes an air pump in operational communication with the first balloon. The system where the control unit includes an oxygenator in operational communication with the primary lumen. The system where the control unit includes a pump in operational communication with the oxygenator and primary lumen. The system further including a pressure gauge configured to measure pressure between the aorta and inferior vena cava. The system where the inflation and deflation of at least one of the aortic balloon or the venous balloon can be controlled by the pressure gauge. The system further including a control unit including an oxygenator, where the oxygenator is in fluidic communication with the heart of the patient by way of the first and second catheters. The system where the control unit further includes at least one air pump in gaseous communication with the aortic balloon and venous balloon.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed and contemplated herein relate to a catheter adapted to be quickly positioned within the body of a patient for use in resuscitation.

As shown generally in the figures, various implementations of the system 1 have a catheter 10 or catheters 10, 100 can be inserted into a region of the vascular system of a patient—such as into the aorta and/or vena cava—to occlude and/or perfuse the region. While the discussion of FIGS. 1A-5B primarily focuses on the structure and function of a catheter 10 inserted into the aorta, and the catheter 10 can function in similar fashion when placed in the inferior or superior vena cava. In exemplary embodiments, as discussed in relation to FIGS. 1B and 6A-C, a venous catheter 100 can be provided. In each of the disclosed embodiments, the catheter 10, 100 can be used to isolate a portion of the vascular system, as is shown in FIGS. 4A-6C. As would be apparent to one of skill in the art, each of the disclosed embodiments of the catheter 10, 100 can be used in either the aorta, vena cava, or other portion of the circulatory system as required.

Figure 1A:
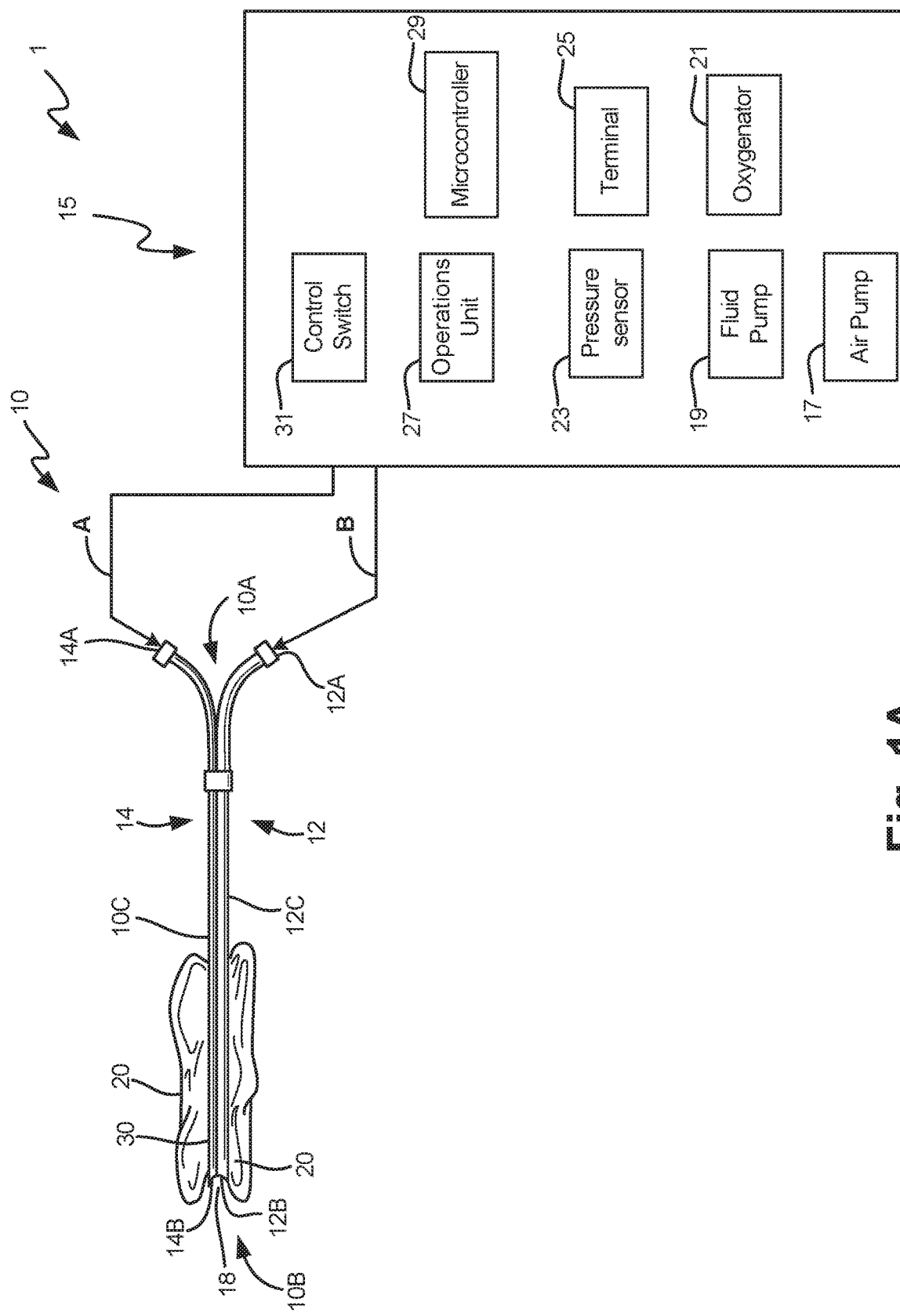
FIG. 1A is a schematic diagram of the catheter system with one catheter and a control unit, according to an exemplary embodiment.

One embodiment, shown in FIG. 1A, is a multi-lumen balloon catheter 10 with an elongate, flexible tubular catheter shaft 10C and at least one primary lumen 12 defined within the catheter shaft 10C capable of perfusing a region of the circulatory system. As shown in the implementation of FIG. 1A, at least one supplemental lumen 14 is provided within the shaft 10C, with certain embodiments, like that of FIGS. 2A-B, having a second supplemental lumen 16.

Figure 2A:
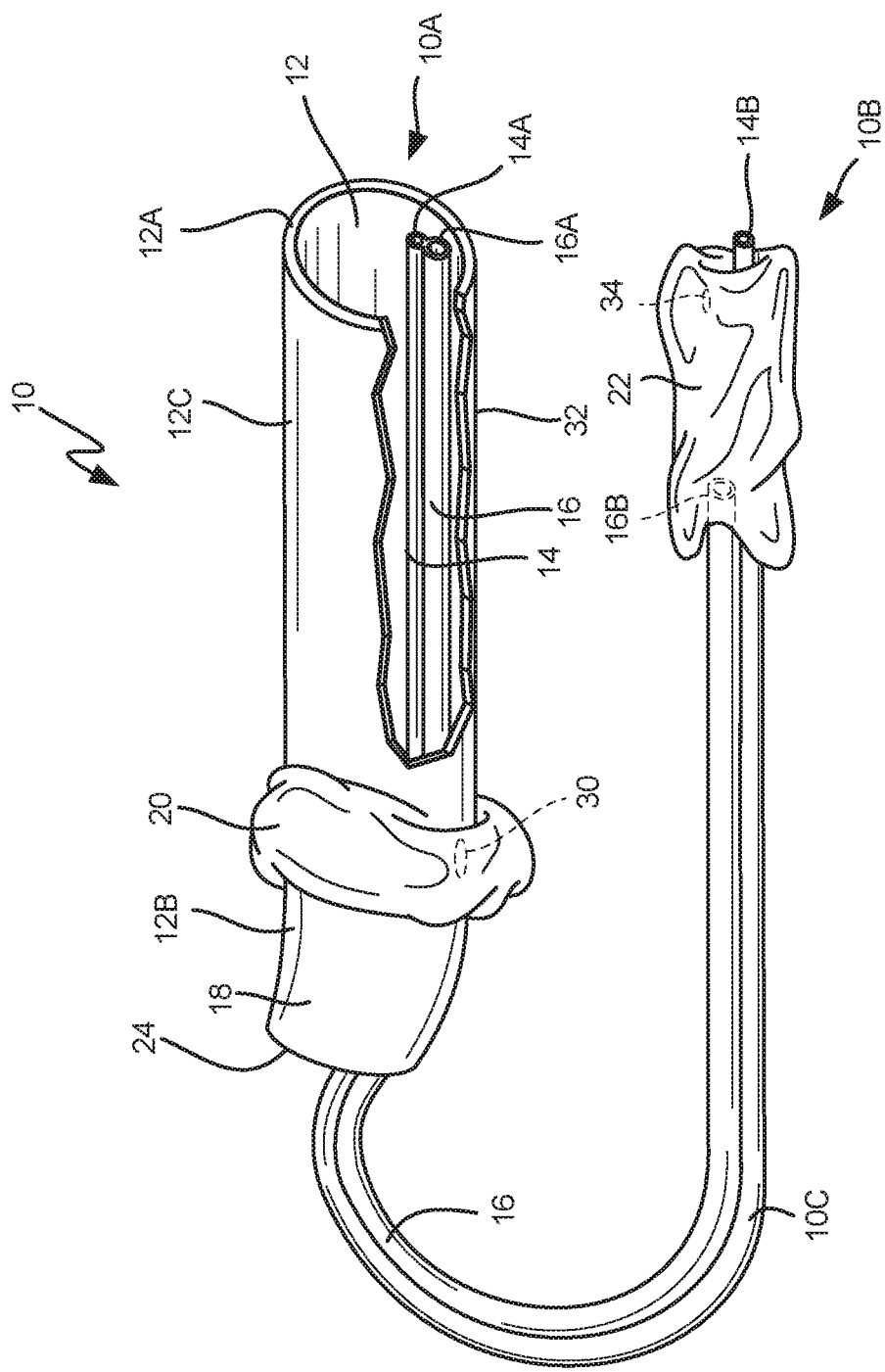
FIG. 2A is a cutaway side-view of an embodiment of the catheter having at least one fixed supplemental lumen.
Figure 2B:
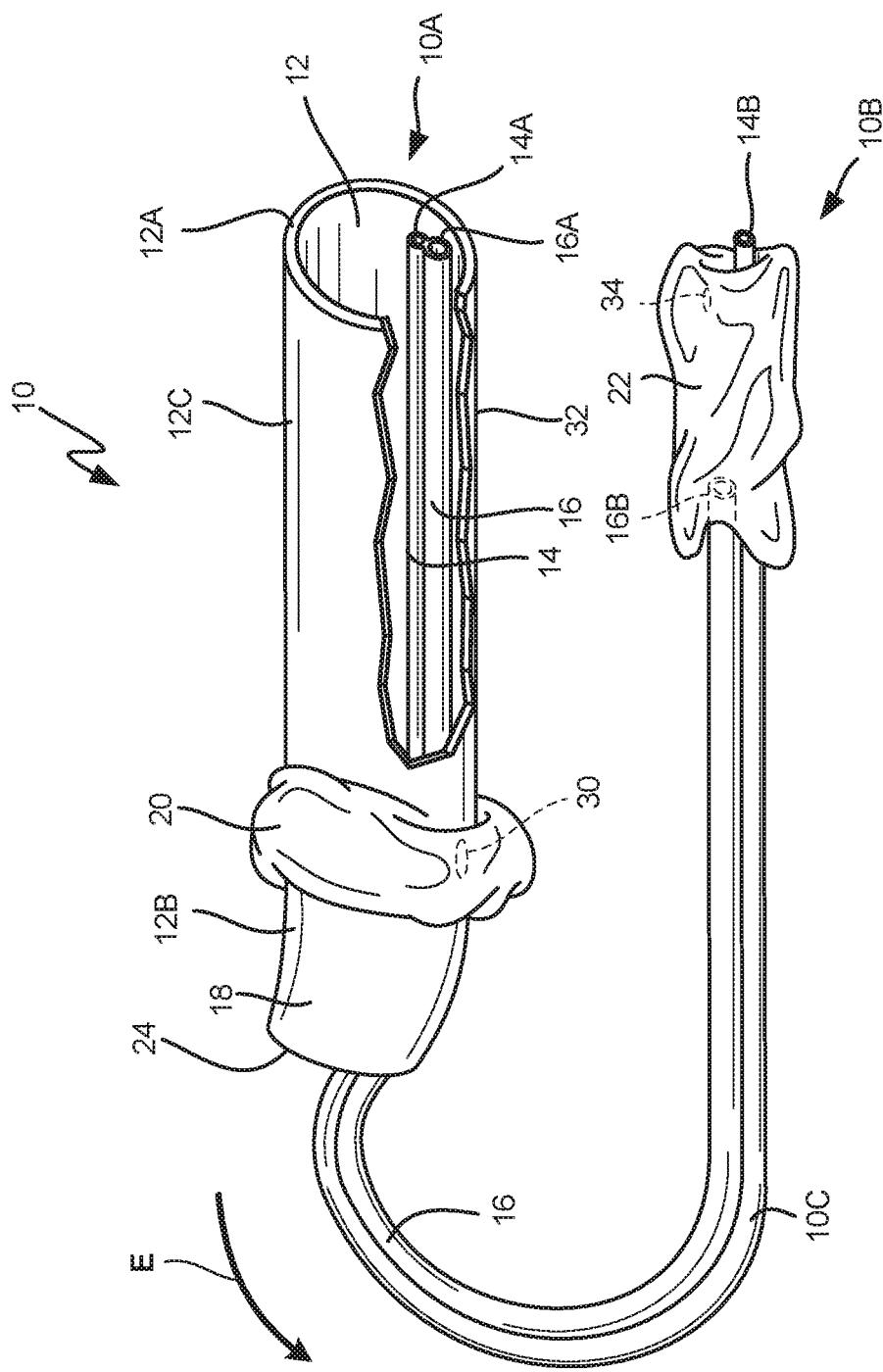
FIG. 2B is a cutaway side-view of an embodiment of the catheter having at least one fixed supplemental lumen.

Returning to FIG. 1A, the supplemental lumen 14 (or lumens 16) can be configured to be extended through an opening 18 at the distal end 12B of the primary lumen 12, as is shown in FIGS. 2A-B. As discussed further in relation to FIGS. 2A-B, in certain embodiments the supplemental lumens 14, 16 are fixedly attached to the internal wall of the primary lumen 12. In alternate embodiments, and as discussed in relation to FIGS. 4A-B, the supplemental lumens 14, 16 are freely extendable relative to the primary lumen 12, so that the supplemental lumens 14, 16 can be "threaded" through the primary lumen 12 and extended into the circulatory system.

Additionally, in implementations like that of FIG. 1A, the catheter 10 has at least one balloon 20 capable of being inflated to occlude the flow of blood in a portion of the circulatory system—such as the aorta or vena cava—so that the heart can be perfused by a lumen such as the primary lumen 12, as is described herein. In the implementation of FIG. 1A, the balloon 20 is in hermetic communication with the first supplemental lumen 14, but other configurations are possible.

Figure 1B:
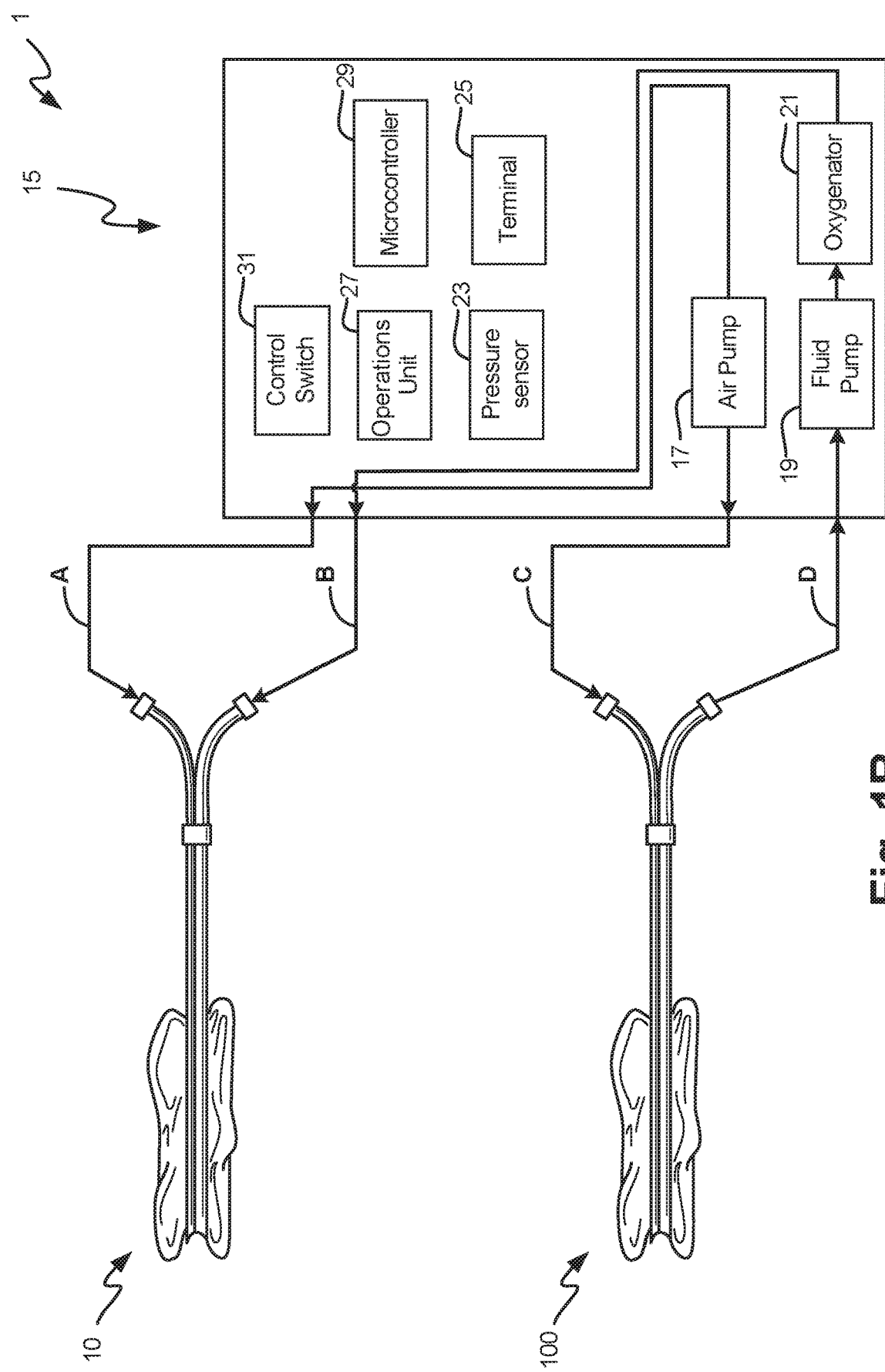
FIG. 1B is a schematic diagram of the catheter system with two catheters and a control unit, according to another exemplary embodiment.

As shown in FIG. 1B, in certain embodiments a second catheter 100 can also be provided, such that a patient can be catheterized contemporaneously in multiple locations—such as the aorta and vena cava—by the catheters 10, 100. As discussed herein, the first catheter 10 may be referred to as the "aortic catheter" and the second catheter 100 as the "venous catheter," but this is in no way intended to be limiting—the catheters 10, 100 can be disposed in any order. These multiple-catheter implementations allow the system 1 to quickly and easily occlude and perfuse a region of the circulatory system by way of the first catheter 10 and second catheter 100, as is described below in reference to FIGS. 6A-C. In these embodiments, the first catheter 10 and second catheter 100 (or aortic catheter 10 and venous catheter 100), are capable of being disposed so as to occlude and perfuse a region of the heart (shown generally at 50 in FIGS. 4A-6C).

Continuing with FIGS. 1A-B, various implementations of the catheter 10 are generally elongate and have a proximal catheter end 10A and a distal catheter end 10B, which is configured for insertion into the patient, as described below. In the implementation of FIG. 1A, the catheter 10 also has an elongate catheter shaft 10C and a plurality of lumens, namely a primary lumen 12 having a proximal primary lumen end 12A and distal primary lumen end 12B, and a first supplemental lumen 14 having a proximal first supplemental lumen end 14A and distal first supplemental lumen end 14B. In exemplary embodiments, the supplemental lumen 14 can be disposed within the end 14B can extend past the distal primary lumen end 12B, as is shown for example in the embodiment of FIG. 2A.

As best shown in FIGS. 1A-B, the first lumen 12 also has a body 12C, which in certain implementations is monocoque, meaning that it provides its own structural rigidity and can be coextensive with the proximal portion of the catheter shaft body 10C. As is described below, in certain embodiments, the body 10C can be coextensive with portions of the primary lumen 12 and certain distal aspects of any supplemental lumens 14, 16. In alternate embodiments, the primary lumen 12 can be disposed within the catheter body 12C. In various implementations, the first lumen 12 further comprises a substantially tubular and malleable housing, or body 12C to prevent excessive compression and retain both rigidity and flexibility, as is well-known in the art. In various implementations, the primary lumen 12 allows for passage of procedure fluids, instruments through an opening 18 disposed near the distal catheter end 10B. Each of the body 10C and various lumens 12, 14 can be formed from materials currently used in cardiac and vascular catheters, including nylon, polyurethane, polyethylene, PVC or other polymers and materials known in the art. The balloon 20 can be made of nylon, polyurethane or polyethylene derivative.

In various catheter implementations, such as that of FIGS. 1A-B, a valve 30 or other opening can be disposed near the distal catheter end 10B to selectively inflate the balloon 20 from air supplied by a lumen, as described further herein. In the implementation of FIG. 1A, the balloon 20 is in hermetic communication with the first supplemental lumen 14, but other configurations are possible. In the implementation of FIG. 1A, for example, the first supplemental lumen 14 is in corresponding hermetic communication with the external operations system, or control unit 15 air pump 17.

In certain implementations, such as those of FIGS. 2A-3E, the catheter 10 has a plurality of balloons 20, 22. In further implementations, the primary lumen 12 is configured to deliver oxygenated blood to the patient, and at least one supplemental lumen 14, 16 is configured to provide additional support, such as inflating the balloon 20 or balloons 20, 22 as described herein. Accordingly, in exemplary embodiments, one or both of the supplemental lumens 14, 16 is in sealed hermetic and fluidic communication with the balloon 20 and/or the second balloon 22.

As is shown in the implementations of FIGS. 1A-B at reference arrows A, B, C and D, air (reference arrows A and C) and fluid, such as blood (reference arrows B and D) are able to be passed to and from the various catheter lumens 12, 14, 16 by way of the control unit 15. In the implementations of FIGS. 1A-B, an control unit 15 having an air pump 17 in operational communication with the catheter 10 may be provided. A circumferential balloon 20 may also be inflated through the opening, using for example, the air pump 17. As shown in FIGS. 1A-B, the control unit 15 can also house various additional external components. These external components can include: a fluid pump 19, such as a centrifugal or peristaltic pump, which is in operational communication with the primary lumen and an external membrane oxygenator 21, a pressure sensor 23, a terminal 25 and other equipment which would be apparent to one of skill in the art.

In various implementations, and as shown in FIG. 1B, the fluid pump 19 is also in operational communication with the connected a venous catheter 100 to withdraw blood and deliver it to the external oxygenator 21. Correspondingly, the external oxygenator 21 can be configured to receive and oxygenate blood from the fluid pump 19 and infuse it back to the body through the primary lumen 12 of the catheter 10 (shown by reference arrows B and D in FIG. 1B and at 90 in FIG. 4A). Further, the pressure sensor 23 can be provided and connected to one or more of the lumens 12, 14, 16 to measure concomitant changes internal balloon 20, 22 and/or internal lumen 12, 14, 16 pressure.

Continuing with the implementations of FIGS. 1A-B an inflation/deflation operations unit 27 can be provided on the control unit 15, the inflation/deflation operations unit 27 configured to control the inflation of the various balloons 20, 22 by way of the air pump 17, as is indicated at reference arrows A and C. As described below, for example in FIG. 6A, after placement of the catheter 10 or catheters 10, 100, the various balloons 20, 120 can be inflated by the air pump 17 to occlude a region of the circulatory system (shown generally at 200). Following this occlusion, the various lumens 12, 112 can serve to perfuse the region with oxygenated blood and recirculate blood by way of the fluid pump 19 and oxygenator 21, as is indicated at reference arrows B and D in FIG. 1B and described further herein.

In certain implementations a pressure gauge 24 (also shown in relation to FIGS. 2A-B and 5A) is connected to a lumen to measure the pressure in the area of aorta between the occlusive balloons 20, 22, and in certain implementations directly control the inflation or deflation of the balloons upon the satisfaction of certain parameters. In various implementations, a microcontroller 29 and control switch 31 can also be provided to effectuate some or all of the discussed functions and external components. The function of these various external components of the control unit 15 is discussed further in relation to FIGS. 5A-6C.

Returning to the structure of the catheter 10, as shown in FIGS. 2A-B, in certain implementations, a second supplemental lumen 16 can also be provided. In the implementations of both FIGS. 2A-B, the catheter 10 has three lumens: a primary lumen 12, a first supplemental lumen 14, and a second supplemental lumen 16. The first supplemental lumen 14 and second supplemental lumen 16 are disposed substantially coaxially within the first lumen 12, though not necessarily concentrically, so as to pass through the primary lumen 12 and extend substantially past the distal end 12B of the first lumen 12 by way of an opening 18.

In various implementations, the first supplemental lumen 14 has a proximal first supplemental lumen end 14A and distal first supplemental lumen end 14B, and the second supplemental lumen has a proximal second supplemental lumen end 16A and distal second supplemental lumen end 16B. In the implementation of FIG. 2A, the first supplemental lumen 14 and second supplemental lumen 16 are disposed substantially within the primary lumen 12 such that the first supplemental lumen 14 and second supplemental lumen 16 are fixed relative to the primary lumen 12, whereby the distal first supplemental lumen end 14B and distal second supplemental lumen end 16B form the distal end of the catheter body 10C and the primary lumen 12 forms the proximal end of the catheter body 10C. Other configurations are possible.

For example in the implementation of FIG. 2B, following placement of the primary lumen 12, the supplemental lumens 14, 16 can be extended through the opening 18 through the application of force to the proximal lumen ends 14A, 16A, so as to pass through the opening 18 through the aortic arch 54 toward the left ventricle 60, as is shown in relation to reference arrow E in FIG. 2B.

Continuing with the implementations of FIGS. 2A-B generally, the first supplemental lumen 14 and second supplemental lumen 16 extend substantially the length of the catheter 10, and the first lumen 12 is disposed substantially at the proximal catheter end 10A, substantially housing the proximal first supplemental lumen end 14A and proximal second supplemental lumen end 16A. Other configurations are possible, as would be apparent to one of skill in the art. In embodiments with this configuration the catheter system further comprises a descending aortic balloon 20 and a valve 30, which in operation can be used to selectively inflate the balloon 20 from air supplied by a lumen, here the second supplemental lumen 16, as is shown in FIG. 2B.

In the embodiments of FIGS. 2A-B, the multiple lumen configuration can facilitate blood flow and provide the user healthcare provider with treatment options. Accordingly, various embodiments further comprise a plurality of circumferential balloons 20, 22. In exemplary embodiments, the primary lumen 12 generally functions to facilitate patient cerebral and coronary circulation. The first supplemental lumen 14 operates to provide user access to various areas of the heart, such as the left ventricular cavity 60 (as is shown in FIGS. 4A-5B). By way of example, in certain embodiments, the first supplemental lumen 14 can be used to deliver medications, instruments and/or other supplies that may be desired. The second supplemental lumen 16 is in hermetic and fluidic communication with both the first, or aortic balloon 20 and second, or ventricular balloon 22. In the embodiment of FIGS. 1-2, the distal supplemental lumen opening 26 is disposed at or near the distal second supplemental lumen end 16B and is in hermetic and fluidic communication with the second balloon 22, so as to be capable of inflation and deflation of the second balloon 22. In various implementations, gas and/or fluid can be used to inflate the various balloons 20, 22, such as by way of the air pump 17 depicted in FIGS. 1A-B.

As would be apparent to one of skill in the art, before and/or after inflation of the balloon 20, the catheter 10 can also be used for infusion of blood and/or other procedures fluids by way of the various lumens 12, 14, 16 so as to restore normal blood flow in the patient. In addition to serving as a conduit for fluids and oxygen in certain implementations, certain lumens 12, 14, 16 can also serve as a means for the delivery of surgical tools, medications, fluids and the like. In any event, the catheter 10 is configured so as to aid in the return to normal cardiopulmonary function in a patient.

As discussed in relation to FIGS. 2A-B, the aortic balloon 20 can be inflated by way of the valve 30 and valve operator 32, such as a thread or guidewire. In certain embodiments, both balloons can be attached by way of a lumen or plurality of lumens so as to eliminate the need for the valve 30. Further configurations forgo a valve, and are configured such that both the first, or aortic balloon 20 and second, or ventricular balloon 22 can inflate and deflate substantially simultaneously. Yet another configuration comprises a further lumen so as to supply air to the ventricular balloon 22 and thus eliminating the need to such flow control valve 30.

Figure 3A:
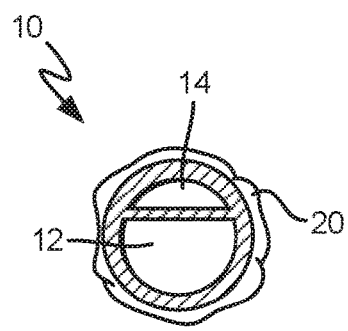
FIG. 3A is cross-sectional view of the catheter, according to one exemplary embodiment.
Figure 3B:
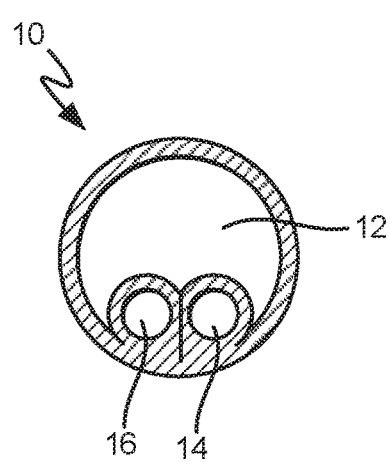
FIG. 3B is cross-sectional view of the catheter, according to another exemplary embodiment.

As best shown in FIG. 3A, in implementations of the catheter 10 having a primary lumen 12, the first supplemental lumen 14 can be disposed within or adjacent to the primary lumen 12 and configured inflate the balloon 20, which is disposed radially around the catheter 10 and lumens 12, 14. As best shown in FIG. 3B, the first supplemental lumen 14 and second supplemental lumen 16 can also be disposed within the primary lumen 12.

Figure 3C:
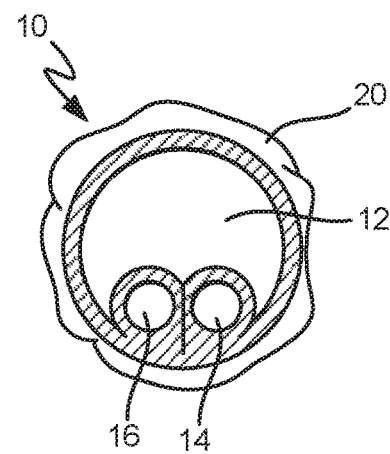
FIG. 3C is cross-sectional view of the catheter, according to another exemplary embodiment.
Figure 3D:
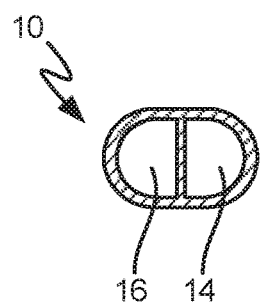
FIG. 3D is cross-sectional view of the catheter, according to another exemplary embodiment.
Figure 3E:
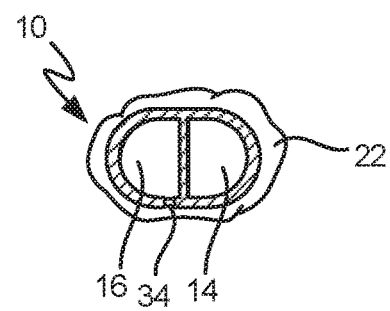
FIG. 3E is cross-sectional view of the catheter, according to another exemplary embodiment.
Figure 4A:
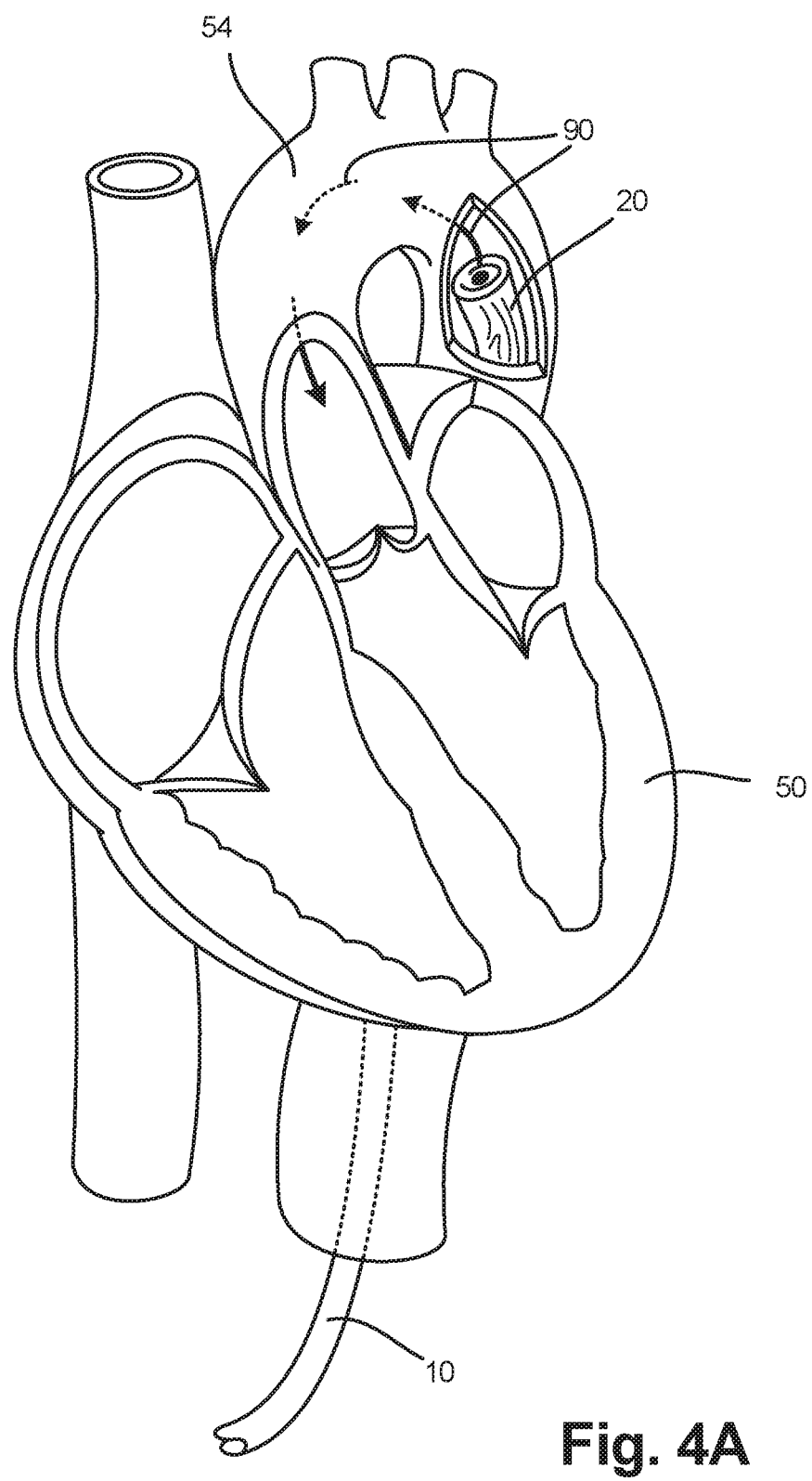
FIG. 4A is a cutaway view of a heart showing the catheter placed in the heart, according to another exemplary embodiment.
Figure 4B:
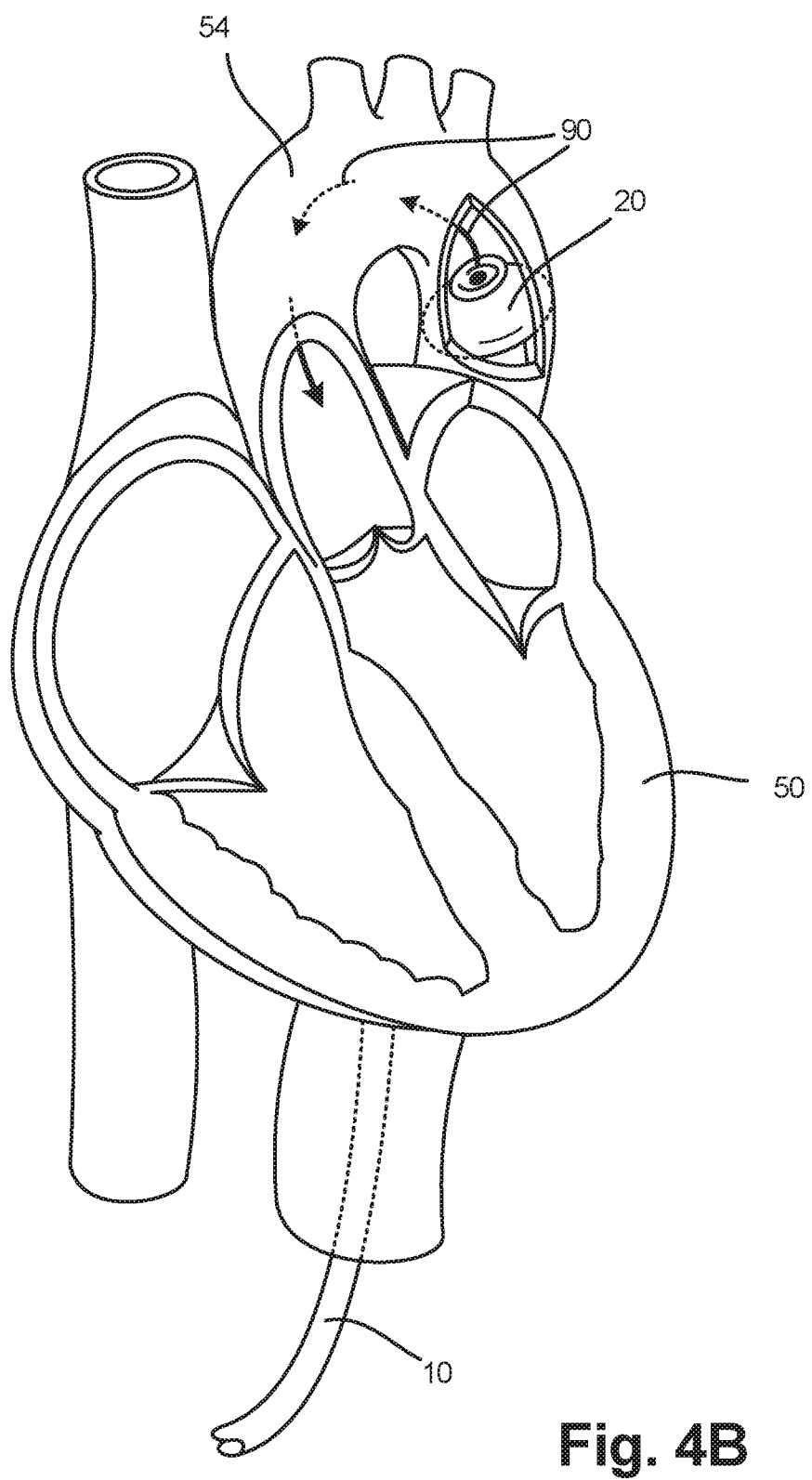
FIG. 4B is a cutaway view of a heart showing the catheter of FIG. 4A wherein the balloon has been inflated.
Figure 4C:
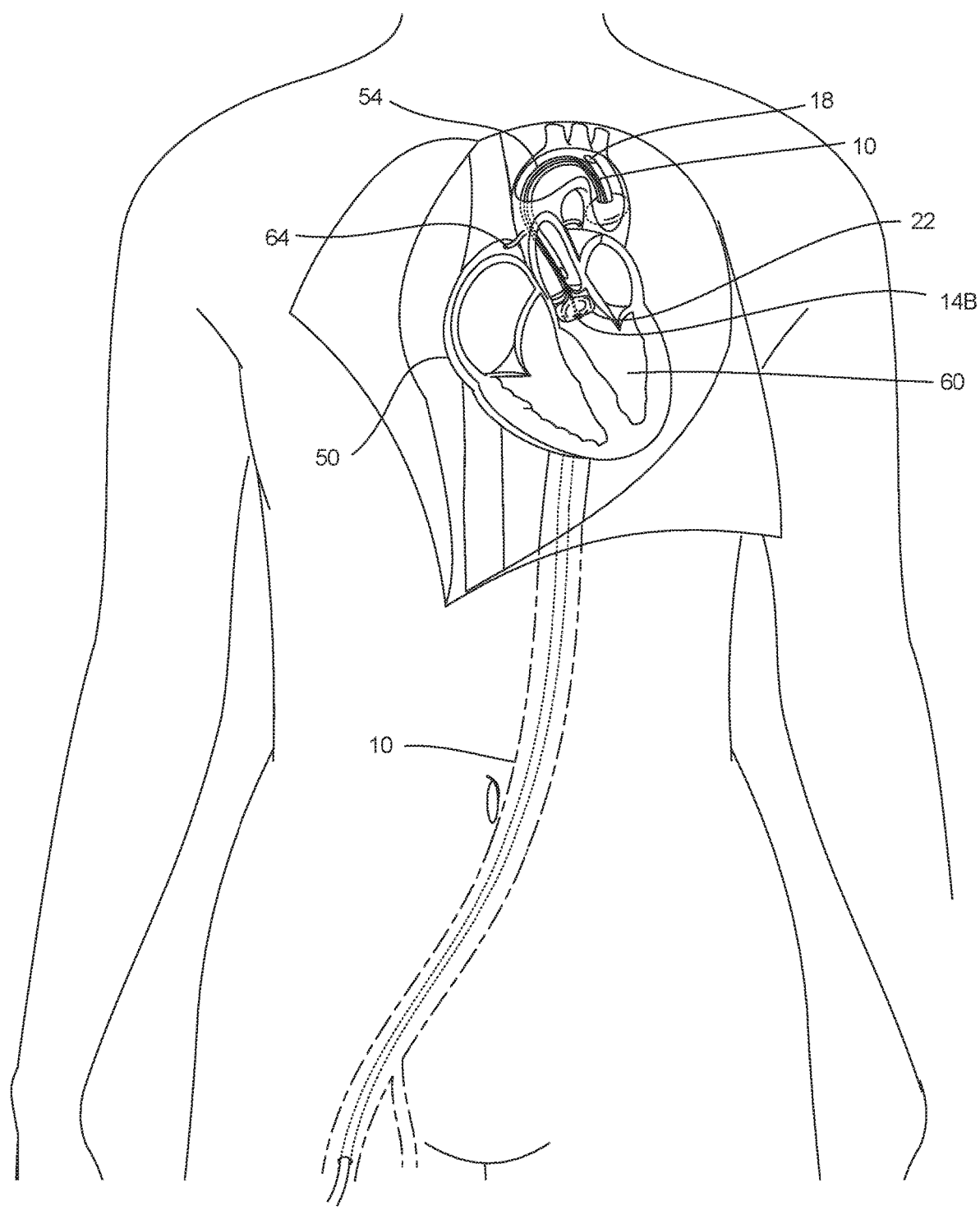
FIG. 4C is a cutaway view of the catheter disposed within the patient, according to another exemplary embodiment.

As shown in FIG. 3C, the second supplemental lumen 16 comprises a valve 30 which controls the flow of gasses and fluids to the first balloon 20. After exiting the opening (not shown), the first supplemental lumen 14 and second supplemental lumen 16 can be disposed within the heart 50. In certain implementations, a distal valve 34 is provided at the distal end of one of the supplemental lumens 14, 16 and is in operational communication with a second balloon so as to promote the inflation or deflation of the second balloon 22.

As shown in FIGS. 4A-5B, in certain implementations, the catheter 10 can be introduced into the femoral artery of a person undergoing CPR by utilizing a modified Seldinger technique, as is well-known in the art. The catheter 10 can be thereby be disposed within the aorta 54 so as to introduce the balloon 20 or balloons 20, 22 for operation. In certain embodiments, the catheter 10 is sized at about 8-16 Fr, with the primary lumen 12 sized to be about 8.5-10 French ("Fr") or larger, though other sizes are possible. In various further implementations the primary lumen 12 can be between about 8-12 Fr. In various implementations, the first and/or second supplemental lumens 14, 16 can be about 2-3 Fr. Accordingly, in various implementations, the overall catheter 10 can be sized at about 8-16 Fr, depending on the implementation. In any event, the catheter 10 is sized to accommodate between about 500 cc to about 1000 cc of blood per minute through the primary lumen 12, and the supplemental lumens 14, 16 are sized to be able to inflate and deflate the balloon 20 or balloons 20, 22 quickly, as would be apparent to one of skill in the art.

Turning back to the operation of the catheter within the body, FIGS. 4A-5B depict an implementation wherein the catheter 10 has been inserted into the heart 50. In these embodiments, the distal catheter end 10B has been inserted into the heart 50 of the patient by a user during introduction of the catheter 10. In these implementations, an arterial puncture of the right or left femoral artery is performed as per a standard technique, and can be performed using anatomical localization techniques such as a basic vascular ultrasound machine or other devices and systems well-known in the art, such as near infrared technology. The distal catheter end 10B can then be introduced into the femoral artery using modified Seldinger technique and then advanced into the descending aorta 52. In certain embodiments, this procedure can be performed with or without the use of a guidewire. In various alternative implementations, insertion may be achieved by using a different arterial access like the right or left common carotid artery in the neck and then proceeding down to the arch of aorta and then the descending aorta 52 and into the arch of the aorta 54.

As best shown in the implementations of FIGS. 4A-5B, after initially positioning the catheter 10 such that the opening 18 is disposed within the descending aorta 52 or the arch 54, a first balloon 20 can be inflated in the descending aorta 52 below the origin of the left subclavian artery 56. The first supplemental lumen 14 and second supplemental lumen 16 may be passed further past the arch of the aorta 54 and around into the ascending aorta 58. In certain embodiments, this first balloon 20 is in operational communication with the second supplemental lumen 16 so as to be inflated by air passed through the second supplemental lumen 16 and occlude the flow of blood through the descending aorta 54.

Continuing with FIGS. 5A-B, a second balloon 22 may be inflated distally of the right and left coronary arteries 62, 64, for example substantially inside the left ventricle 60 below the aortic valve 66 and mitral valve 74. Other configurations may comprise balloons of various sizes and shapes, for example cylindrical, globe or pear shaped balloons. In these implementations, the left ventricular balloon 22 is thus inflated by the second supplemental lumen 16 so as to be in contact with the left ventricular wall 68 and inter-ventricular septum 76 so as to occlude the outflow tract 80 and the aortic valve 66 and aortic valve opening 82. Exemplary embodiments of the system result in isolation of the portion of the aorta wherein the cerebral and coronary vessels originate. In these embodiments, venous blood is withdrawn using a central venous catheter and then circulated through an external oxygenator and returned using the proposed catheter to the portion of aorta enclosed by the two inflated balloons 20, 22.

Figure 5A:
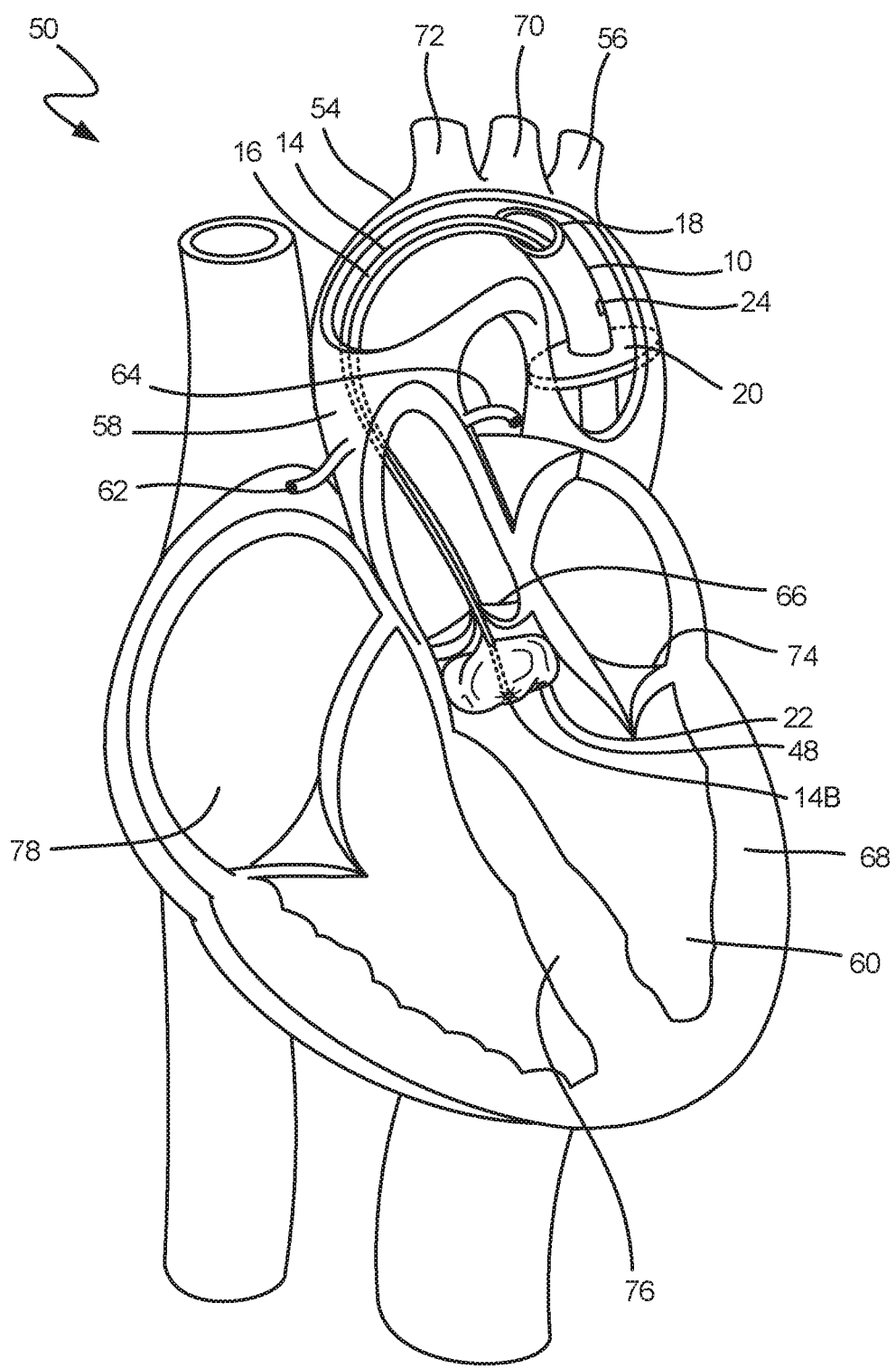
FIG. 5A is a cutaway view of a heart showing the catheter placed in the heart, according to another exemplary embodiment.

FIG. 5A also depicts the aortic balloon 20 as substantially disc-shaped. FIG. 5B depicts a rounded balloon configuration 20. May other implementations are possible. In the embodiment depicted in FIGS. 1-4, the second supplemental lumen 16 is in operable communication with the balloon 20. Other configurations are also possible, such that the second supplemental lumen 16 can be used to inflate the aortic balloon 20.

As discussed in relation to FIGS. 1A-B, the catheter 10 may only contain two lumens, a primary lumen 12 and a first supplemental lumen 14. In these embodiments, the ventricular balloon 22 may be inflated by way of the first supplemental lumen 14. As is depicted in FIGS. 5A-B, in certain embodiments, the aortic balloon 4 is a substantially circumferential balloon. In exemplary embodiments, the aortic balloon may be configured to be capable of substantially surrounding the primary lumen 12 of the catheter 10. In these embodiments, the balloon 22 is configured to be inflatable to form an area of contact with the inner surfaces of the wall 52A, 52B of the descending aorta 52 that results in a complete sealing of the aortic arch 54.

In these implementations, the user is then able to advance the catheter 10 slowly through the aortic valve 66. In certain applications, various known detection techniques such as a trans-thoracic echocardiograms, fluoroscopy, intravascular ultrasounds, electrical sensory methods, pressure sensing, and others may be used to locate the echogenic tip 48 of the catheter 10. In exemplary uses, the echogenic tip 48 should be stopped once it has entered the left ventricular cavity 60. The descending aortic balloon 20, which in exemplary embodiment is located just below the root of the left subclavian artery 56 along with opening 18, is inflated using airflow coming through the second supplemental lumen 16, and generated by an air pump 17 located in a control unit 15 (as is shown in FIGS. 1A-B).

Figure 5B:
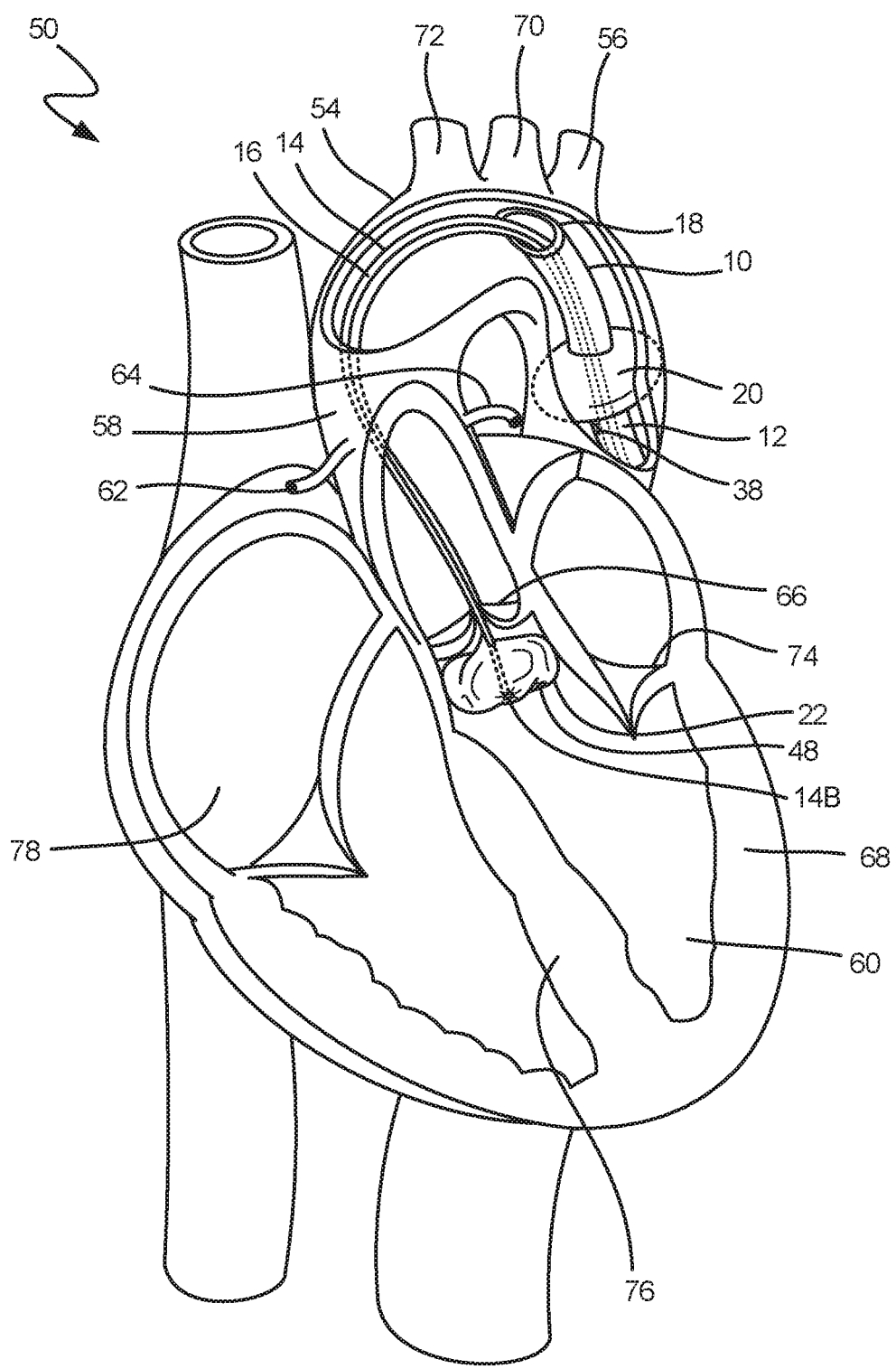
FIG. 5B is a cutaway view of a heart showing the catheter placed in the heart, according to another exemplary embodiment.

Continuing with FIGS. 5A-B, following proper catheter 10 insertion, occlusion of the descending aorta 52 serves to substantially prevent blood flow from the aortic arch 54 to the lower body. In these embodiments, occlusion—and the corresponding flow of gas or fluid into the aortic balloon 22 can be monitored through a pressure sensor 24 connected to the second supplemental lumen 16 and located in the control unit 15. As shown in FIGS. 1A-B, in such embodiments, the external blood pump 19 located in the control unit 15 may be toggled between on and off positions by way of a control switch 31, so as to facilitate the withdrawal of blood from the venous side, in certain embodiments by way of one or more additional venous catheters 100, as discussed herein in relation to FIGS. 6A-C.

Figure 6A:
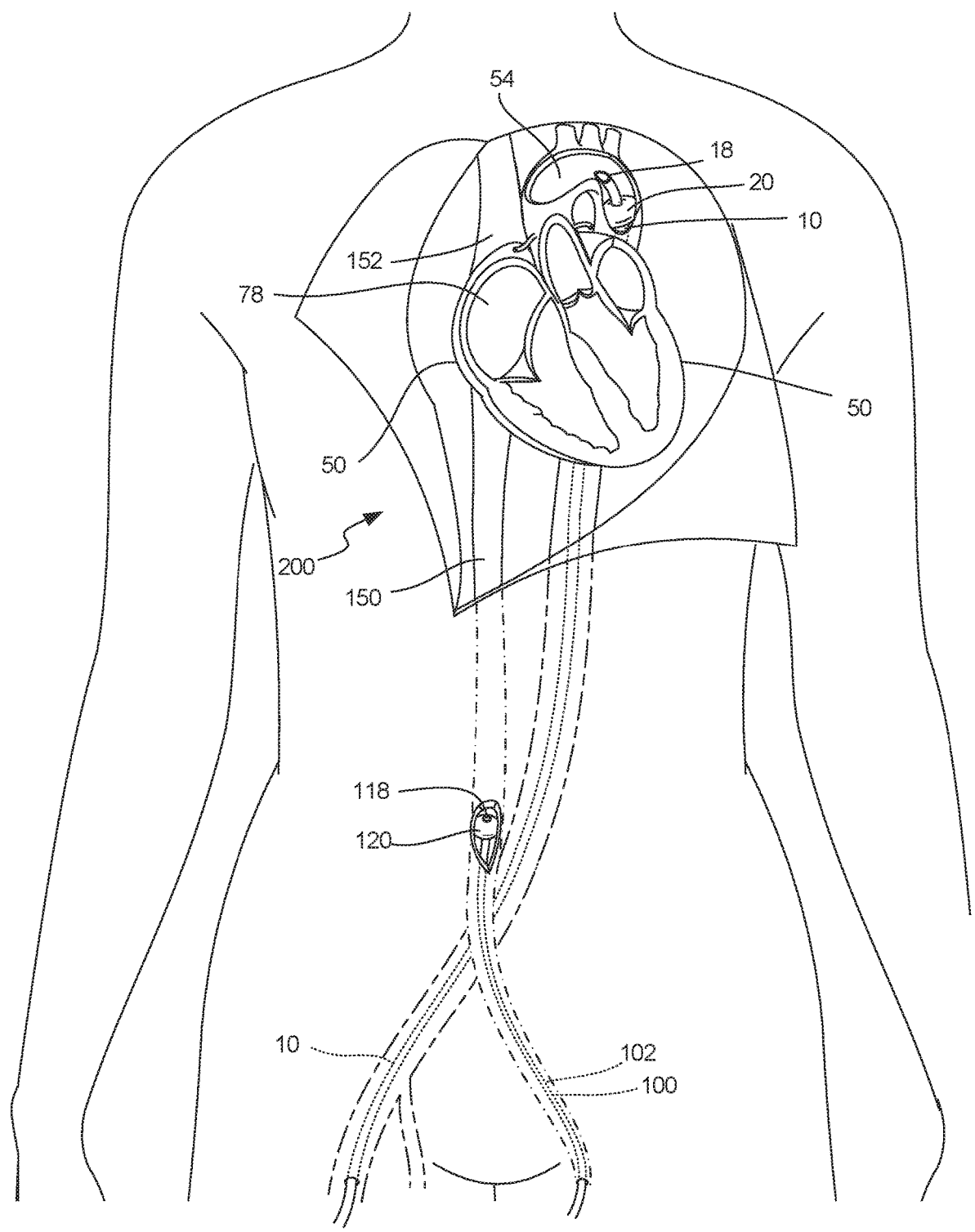
FIG. 6A is a cutaway view of a catheter disposed within the aorta and a catheter disposed within the inferior vena cava of a patient, according to one exemplary embodiment.
Figure 6B:
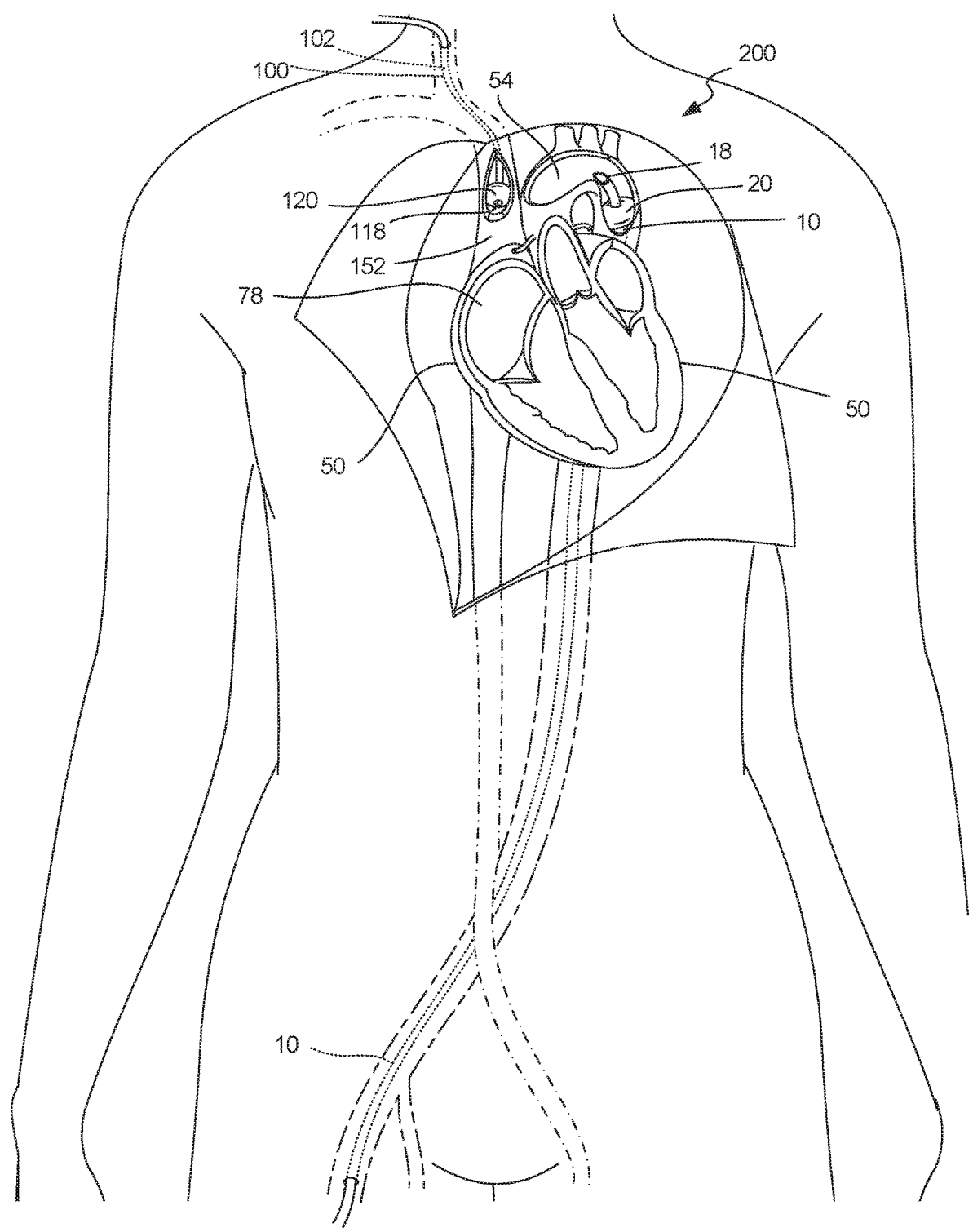
FIG. 6B is a cutaway view of a catheter disposed within the aorta and a catheter disposed within the superior vena cava of a patient, according to one exemplary embodiment.
Figure 6C:
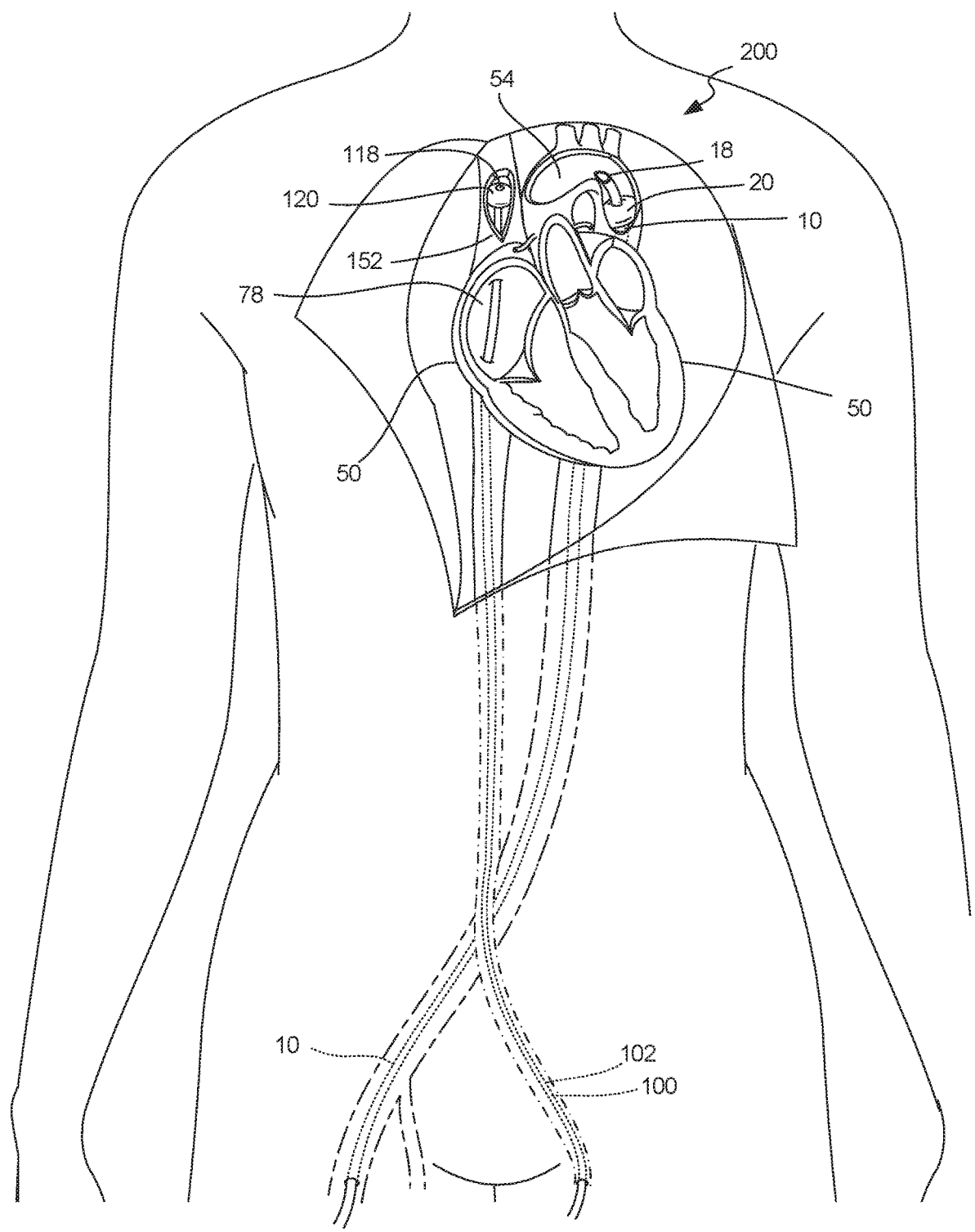
FIG. 6C is a cutaway view of a catheter disposed within the aorta and a catheter disposed within the superior vena cava of a patient, according to another exemplary embodiment.

The implementations of FIGS. 6A-6C depict further embodiments of the system 1 with a catheter 10 and a venous catheter 100 being used to oxygenate the blood of the heart 50. In these implementations, the venous catheter 100 comprises at least a primary lumen 102 and supplemental lumen 104, as has been previously described. Further, a venous balloon 120 is provided which is in operational communication with at least one lumen 102, 104 and is configured to occlude the inferior vena cava 150 (shown in FIG. 6A) or superior vena cava 152 (shown in FIGS. 6B-C) as has been previously described above in relation to the aorta 54.

In these embodiments, and as shown in FIGS. 6A-6C, at least one venous opening 118 capable of receiving the is thereby disposed in the inferior vena cava 150 (shown in FIG. 6A) or superior vena cava 152 (shown in FIGS. 6B-C). This venous opening or openings 118 can be disposed distally or proximally on the catheter shaft or primary lumen 102 relative to the balloon 120 and be configured to facilitate the withdrawal of blood from the venous side.

In conventional applications, venous catheters are relatively large and are usually positioned very high: near or inside the right atrium 78. This placement is used to prevent any suction events. Because the venous catheter 100 is only used to draw blood at a low rate of around 1 liter/min, and given that it is lined by an inflated balloon that supports the venous wall 150 and preventing its collapse, in various implementations, the venous catheter 100 can be positioned lower in the inferior vena cava 150, which allows for use of a smaller catheter 100.

In certain implementations of the system 1, and as shown in FIGS. 6A-C, the venous catheter 100 and aortic catheter 10 can both be in operational communication with the control unit 15, as is described in relation to FIG. 1B. In exemplary implementations, the operation of the aortic balloon 20 and venous balloon 120 can be coordinated, such that the inflation and deflation of the balloons happens simultaneously. Accordingly, the region (shown generally at 200) between the aortic balloon 20 and venous balloon 120 can be occluded, such that that oxygenated blood may be passed from the aortic primary lumen 12 through the heart 50 and back into the venous catheter 100. Upon exiting the venous catheter, the blood can be passed through the control unit 15 and oxygenator 21, and correspondingly re-introduced into the heart by the aortic catheter 10.

In use, the catheter 10 facilitates the circulation of blood through the external membrane oxygenator 21 (as shown on the control unit 15 of in FIGS. 1A-B). Oxygenated blood 90 can then be circulated away from the oxygenator using another pump 19, such as a centrifugal pump 19, located in the control unit 15. This oxygenated blood 90 can then be returned to the patient through the primary lumen 12. In certain embodiments, oxygenated blood 90 may be carried under pressure in the primary lumen 12 until it reaches the descending aortic balloon 20 and exits through the opening 18. As would be apparent to one of skill in the art, the opening 18 can be disposed near the roots of the left subclavian artery 56, left common carotid artery 70 and/or innominate artery 72. Correspondingly, the left ventricular balloon 22 can be inflated using airflow exiting through the second supplemental lumen 16, so as to occlude the left ventricular outflow tract 60.

In certain implementations, a pressure gauge 24 can be disposed on the shaft or tip of the aortic catheter 10 and is configured to monitor blood pressure trends. In various implementations, once blood pressure indicates the return of the normal cardiac function, the pressure gauge 24 can be configured to signal the control unit to deflate both the one or more balloons 20. Further, if the heart is functioning but the blood pressure remains very low, the catheter 10 can be configured to provide circulatory support by withdrawing blood from the venous side and infusing it into the aorta 54 with or without inflation/deflation of the balloons.

In certain implementations, the catheter 10, 100 also provides a means to measure any changes in the intraventricular pressure, as described above in relation to the pressure gauge 24, thereby allowing the practitioner to detect the return of spontaneous cardiac contractions (not shown). In these embodiments, the system is capable of detecting changes in the ventricular balloon caused by the contraction of the heart, and thus allows the detection of the return of spontaneous heart contraction. In certain implementations, one of the lumens allows direct access to the left ventricular cavity that can be used to introduce pacer-defibrillator leads, or any other instruments.

Although the present invention has been described with reference to preferred embodiments, persons skilled in the art will recognize that changes may be made in form and detail without departing from the spirit and scope of the invention.

What is claimed is:

1. An aortic catheter comprising:
   a. a first elongate, substantially tubular primary aortic lumen having proximal and distal ends and comprising at least one aortic opening at the distal end;
   b. at least one elongate substantially tubular supplemental aortic lumen disposed within the primary aortic lumen and constructed and arranged to extend substantially past the at least one distal aortic opening;
   c. at least one aortic balloon in fluidic communication with the at least one supplemental aortic lumen so as to be inflated by way of the supplemental aortic lumen
   d. a pressure sensor configured to measure changes in aortic pressure,
   wherein the aortic catheter is constructed and arranged to:
   i. be disposed within the aorta of a patient,
   ii. inflate the at least one aortic balloon in response to measured changes in aortic pressure, and
   iii. isolate a portion of the vascular system of the patient.

2. A catheter system, comprising:
   a. the aortic catheter of claim 1; and
   b. a vena cava catheter constructed and arranged to be disposed within the vena cava of the patient and comprising:
      i. a first elongate, substantially tubular primary venous lumen having proximal and distal ends and comprising at least one venous opening at the distal end;
      ii. at least one elongate substantially tubular supplemental venous lumen constructed and arranged to extend substantially past the distal venous opening; and
      iii. at least one venous balloon in operational communication with the at least one supplemental venous lumen so as to be inflated by way of the supplemental venous lumen.

3. The catheter system of claim 2, further comprising a pressure sensor constructed and arranged to measure pressure in the aorta or inferior vena cava.

4. The catheter system of claim 2, constructed and arranged for perfusing the heart of the patient via a control unit in operational communication with the catheters.

5. The catheter system of claim 4, wherein the control unit is constructed and arranged to provide blood in response to the measured pressure.

6. The catheter system of claim 3, wherein the inflation and deflation of at least one of the aortic balloon or the venous balloon can be controlled by the pressure sensor.

7. A cardiopulmonary resuscitation catheter system for use in a patient to permit isolation of a portion of the vascular system of the patient, the system comprising:
 a. a resuscitation catheter comprising:
  i. an elongate primary lumen, comprising:
   A. a proximal primary lumen end;
   B. a distal primary lumen end; and
   C. at least one opening at the distal primary lumen end;
  ii. at least one elongate supplemental lumen disposed within the primary lumen, the supplemental lumen comprising:
   A. a proximal supplemental lumen end; and
   B. a distal supplemental lumen end; and
  iii. at least one balloon constructed and arranged for inflation and deflation;
 b. at least one pressure sensor; and
 c. a control unit comprising an air pump in hermetic communication with the at least one balloon,
 wherein:
  i. the elongate catheter shaft is constructed and arranged to be disposed within the aorta or vena cava of the patient,
  ii. the control unit is constructed and arranged to inflate and/or deflate the at least one balloon, and
  iii. the pressure sensor is constructed and arranged to measure pressure in the aorta or inferior vena cava of the patient such that the inflation and deflation of the at least one balloon can be controlled by the control unit in response to the measured pressure.

8. The system of claim 7, wherein the at least one balloon is in operational communication with the at least one elongate substantially tubular supplemental lumen and inflated by way of the supplemental lumen.

9. The system of claim 7, comprising a second catheter, wherein the first resuscitation catheter is configured to be disposed in the aorta and the second resuscitation catheter is configured to be disposed in the vena cava.

10. The system of claim 7, wherein the at least one balloon comprises a circumferential balloon disposed outside the primary lumen and is constructed and arranged to be inflated in the descending aorta of the patient.

11. The system of claim 10, wherein the second balloon is constructed and arranged to be passed into the ventricular cavity of the patient and inflated.

12. The system of claim 10, wherein the control unit is constructed and arranged to inflate and deflate the first balloon and/or second balloon in response to changes in blood pressure.

13. The catheter of claim 9, further comprising at least one valve in operational communication with the at least one balloon and at least one supplemental lumen, wherein the at least one valve is constructed and arranged to allow passage of fluid or gas into the at least one balloon for inflation and deflation.

14. The catheter of claim 7, wherein the catheter is constructed and arranged to be disposed within the vena cava of the patient.

15. A cardiopulmonary resuscitation system, comprising:
 a. an elongate, tubular catheter constructed and arranged to be inserted through the aortic valve of the patient comprising:
  i. an elongate primary lumen, comprising:
   A. a proximal primary lumen end;
   B. a distal primary lumen end; and
   C. at least one opening at the distal primary lumen end;
  ii. at least one elongate supplemental lumen disposed within the primary lumen, the supplemental lumen comprising:
   A. a proximal supplemental lumen end; and
   B. a distal supplemental lumen end;
  iii. a first balloon disposed outside the primary lumen and adapted for inflation; and
  iv. a second balloon in operational communication with the supplemental lumen;
 b. a pressure sensor configured to measure pressure; and
 c. an external control unit,
 wherein inflation and deflation of at least one of the first balloon or the second balloon is controlled by the external control unit in response to measured pressure.

16. The system of claim 15, wherein the elongate, tubular catheter is constructed and arranged for:
 a. positioning the opening within the descending aorta of the patient;
 b. inflating the first balloon within the descending aorta of the patient via the external control unit; and
 c. inflating the second balloon distally of the right and left coronary arteries of the patient.

17. The system of claim 16, wherein the tubular catheter is further constructed and arranged for regulating the inflation of the first balloon and second balloon in response to changes in blood pressured measured by a pressure sensor.

* * * * *